United States Patent [19]

Wu et al.

[11] Patent Number: 5,182,185
[45] Date of Patent: Jan. 26, 1993

[54] DEEP U.V. PHOTORESIST COMPOSITIONS CONTAINING 4-TERT-BUTYLSTYRENE/MALEIMIDE COPOLYMER AND POLYCYCLIC CYCLOPENTANE-2-DIAZO-1,3-DIONE AND ELEMENTS UTILIZING THE COMPOSITIONS

[75] Inventors: Chengjiu Wu, Morristown; Anne Mooring, Randolph; James T. Yardley, Morristown, all of N.J.

[73] Assignee: Hoechst Celanese Corporation, Somerville, N.J.

[21] Appl. No.: 693,513

[22] Filed: Apr. 30, 1991

Related U.S. Application Data

[62] Division of Ser. No. 373,358, Jun. 29, 1989, Pat. No. 5,039,596.

[51] Int. Cl.[5] .......................... G03F 7/023; G03C 1/61
[52] U.S. Cl. .................................... 430/165; 430/191; 430/192; 430/193; 430/272; 430/277; 430/278
[58] Field of Search ............... 430/191, 192, 193, 165, 430/272, 277, 278

[56] References Cited

U.S. PATENT DOCUMENTS

| | | | |
|---|---|---|---|
| 4,284,706 | 8/1981 | Clecak et al. | 430/191 |
| 4,339,522 | 7/1982 | Balanson et al. | 430/192 |
| 4,522,911 | 6/1985 | Clecak | 430/192 |
| 4,622,283 | 11/1986 | Gray | 430/191 |
| 4,624,908 | 11/1986 | Schwartzkopf | 430/192 |
| 4,626,491 | 12/1986 | Gray | 430/190 |
| 4,735,885 | 4/1988 | Hopf | 430/192 |
| 4,853,315 | 8/1989 | McKean et al. | 430/192 |

OTHER PUBLICATIONS

Chemical Abstracts 89:179563.
Chemical Abstracts 88:152079n.
Chemical Abstracts 87:22505s.
Chemical Abstracts 107:77166u.
Chemical Abstracts 102:184613f.
Chemical Abstracts 99:53746y.
Chemical Abstracts 90:121295s.
Chemical Abstracts 90:103809h.
Chemical Abstracts 89:179563y.
Patent Abstracts of Japan, vol. 3, No. 3(C-33) Jan. 16, 1979, & JP-A-53 127496 (Idemitsu Kosan K.K.).
Chemical Abstracts, vol. 112, No. 4, Jan. 22, 1990, p. 479, Ref. No. 27928B.
I. K. Korobitsyna, Zhi Org. Khim., 12, pp. 1245-1260, 1976.

Primary Examiner—Hoa Van Le
Assistant Examiner—Christopher G. Young
Attorney, Agent, or Firm—Andrew F. Sayko, Jr.

[57] ABSTRACT

Photosensitizers containing saturated and unsaturated polycyclic compounds containing the cyclopentane-2-diazo-1,3-dione structural unit.

These compounds have their maximum u.v. absorption at around 248 nm, decompose into polar products upon irradiation, and can be used as photosensitizers in positive deep u.v. or excimer laser (248 nm) lithography. They are most preferably useful with deep u.v. transparent resins for forming photoresists.

7 Claims, No Drawings

DEEP U.V. PHOTORESIST COMPOSITIONS CONTAINING 4-TERT-BUTYLSTYRENE/MALEIMIDE COPOLYMER AND POLYCYCLIC CYCLOPENTANE-2-DIAZO-1,3-DIONE AND ELEMENTS UTILIZING THE COMPOSITIONS

This is a divisional of copending application Ser. No. 07/373,358, filed on Jun. 29, 1989, now U.S. Pat. No. 5,039,596.

BACKGROUND OF THE INVENTION

The present invention relates to deep u.v. photosensitizers which are polycyclic compounds containing a cyclopentane-2-diazo-1,3-dione structural unit and to photosensitive compositions incorporating these compounds.

Photoresists are materials which change their solubility in a developer solution after it has been exposed to actinic radiation, such as ultraviolet radiation. Photoresist compositions comprise a photosensitive compound, a film forming polymeric resin and a solvent. The photoresist composition is applied to a substrate which is to be patterned and the solvent is then removed, leaving the photoresist as a thin film covering the substrate. As a consequence of the exposure to radiation, a different solubility rate results between imagewise exposed and unexposed portions of a resist film that yields a surface relief pattern after the development. Those photoresists which become more soluble in a developer solution in the exposed regions are referred to as "positive" photoresists. Those which become less soluble in the exposed regions are referred to as "negative" photoresists.

Positive photoresists typically comprise an aqueous alkali soluble resin, such as novolak resin or polyvinyl phenol and a diazonaphthoquinone sulfonic acid ester sensitizer. The resin and sensitizer are supplied such as by spin-coating, spray coating, or other suitable means from an organic solvent or solvent mixture onto a substrate, such as a silicon wafer. After imagewise exposure, the developer removes the non-image areas of the coated photoresist to product a relief pattern in the photoresist film.

It is essential that the mask pattern be accurately reproduced in the substrate etch pattern. To achieve this high degree of accuracy, the mask pattern must be well resolved by the photoresist layer. The laws of optics and diffraction dictate that resolution will improve as the wavelength of the irradiation is shortened. Thus, photoresists capable of operating in the deep ultraviolet region (200-300 nm) will be capable of higher potential resolution than those resists limited to operating in the near ultraviolet region (300-400 nm).

Diazonaphthoquinone sulfonic acid esters are commonly used as sensitizers in conventional near u.v. photoresists. While these ester sensitizers are photoactive in the deep u.v., they exhibit several serious limitations for use as photosensitizers. These sensitizers exhibit intense absorptions in the deep u.v. region, making the resist composition excessively absorptive as well. These deep u.v. absorptions are also poorly photobleached by the exposing radiation so that the film's absorbance is not greatly diminished during the irradiation process. Ideally, the sensitizer photoproduct should be nonabsorbing in the region of irradiation used to expose the resist so that all absorbed light does useful chemistry, thereby maximizing sensitivity. These prior art sensitizers also possess near u.v. absorption bands which allow them to be used in conventional near u.v. photoresists. However, this near u.v. response would be considered a drawback in a true deep u.v. resist, as it would necessitate filtering the exposure source to remove long wavelength radiation to prevent degradation of the resolution.

This invention provides photosensitive compounds and formulations which contain sensitizers designed to operate effectively in the deep u.v. spectral region during the process of integrated circuit manufacture.

Other attempts have been made to design a photoresist system for the deep u.v. region. For example, UK patent Application No. 2,099,168 teaches ortho-nitrobenzyl groups attached to polymers and sensitizer molecules. The use of orthonitrobenzyl chemistry for photoresists is also taught in U.S. Pat. No. 3,849,137.

Chemistry suitable for deep u.v. photoresists also includes that of chain scission of high molecular weight polymer into lower molecular weight polymer. In this case, the energy of the deep u.v. light is sufficient to rupture bonds in the polymer chain, resulting in lower molecular weight material of increased solubility. The most common example of this technique uses poly(methyl methacrylate). The primary drawback of this resist is the need for high exposure doses to yield a sufficient different in molecular weights and the need to use an organic solvent as the developing medium.

Another example of deep u.v. photoresist technology involves the use of deep u.v. excimer lasers of high instantaneous fluence to ablate away selected areas of the photoresist film. This laser photoablation is disclosed in U.S. Pat. No. 4,414,059. Still another disclosure relating to deep u.v. sensitizers is found in European Patent Application 0 129 694, which describes compounds based on diazohomotetramic acid for use in photoresist compositions. U.S. Pat. No. 4,339,522 discloses 5-diazo meldrumacids; EP84 105 544 discloses diazohomotetramic acid compounds. U.S. Pat. No. 4,735,885 discloses deep u.v. photoresists formed from 1,3 disubstituted-5-diazobarbituric acid. Compounds having the 2-diazo-1,3,-dione grouping are also known, as shown in U.S. Pat. No. 4,622,283; 4,284,706; 4,339,522; 4,624,908 and Japanese Patent 78127439. Each of the foregoing has its own shortcoming such as volatility, stability and solubility.

The present invention provides improved compounds based on 5-membered ring structures. They have peak absorptions in the deep u.v. region and are especially sensitive to 248 nm eximer laser radiation.

SUMMARY OF THE INVENTION

The invention provides a photosensitive composition comprising in admixture:
  (a) from about 65% to about 98% based on the weight of the non-solvent parts of the composition of a water insoluble, aqueous alkaline soluble or swellable binder resin; and
  (b) from about 2% to about 35% based on the weight of the non-solvent parts of the composition of a component selected from the group consisting of:

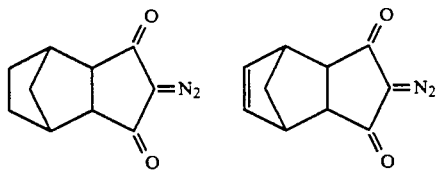 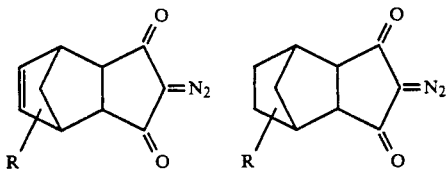

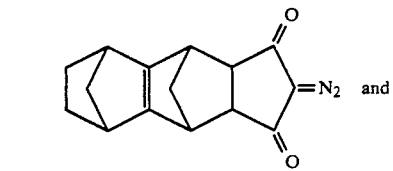 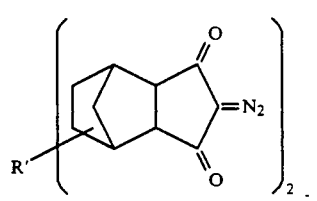

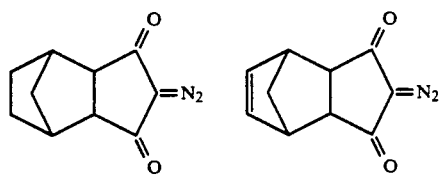

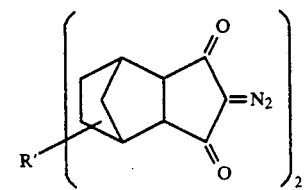

wherein R is $C_6H_{13}$ or $C_{12}H_{25}$ and R' is $-C_{12}H_{24}-$ or

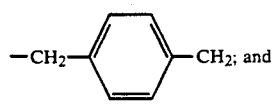

(c) a solvent composition in an amount sufficient to form a substantially uniform admixture of the composition components.

The invention also provides a photographic element which comprises a substrate and the foregoing photosensitive composition substantially uniformly coated on said substrate and dried.

The invention still further provides a process for preparing a photographic image which comprises in order:

i) forming a photosensitive composition comprising in admixture;
  (a) from about 65% to about 98% based on the weight of the non-solvent parts of the composition of a water insoluble, aqueous alkaline soluble or swellable binder resin; and
  (b) from about 2% to about 35% based on the weight of the non-solvent parts of the composition of a component selected from the group consisting of

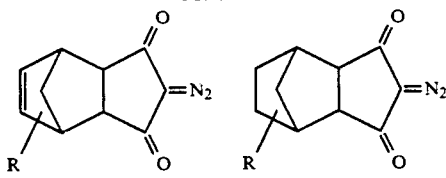 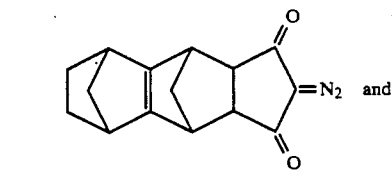

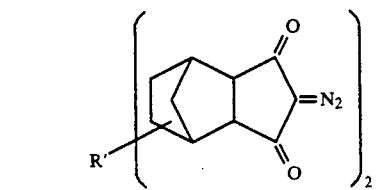

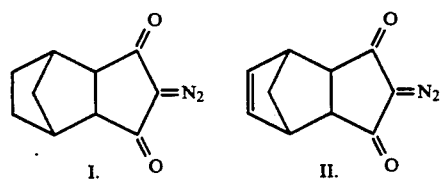

wherein R is $C_6H_{13}$ or $C_{12}H_{25}$ and R' is $-C_{12}H_{24}-$ or

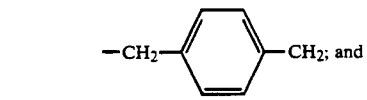

(c) a solvent composition in an amount sufficient to form a substantially uniform admixture of the composition components; and ii) coating said composition on a substrate; and iii) heating said coated substrate at a temperature of from about 20° C. to about 100° C. until substantially all of said solvent is dried off; and iv) imagewise exposing said composition to ultraviolet radiation in the range of from about 200 nm to about 300 nm; and v) removing the non-image areas of said composition with an aqueous alkaline developer solution.

DETAILED DESCRIPTION OF THE PREFERRED EMBODIMENT

One begins the preparation of the photosensitive composition of this invention by preparing one of the following photosensitizers:

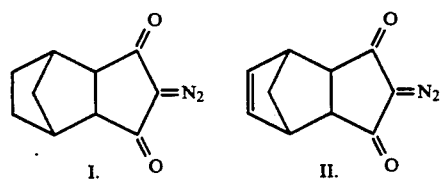

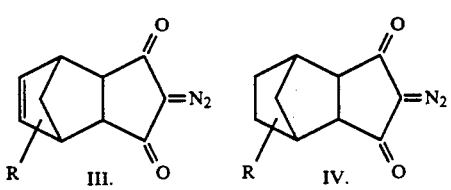

-continued

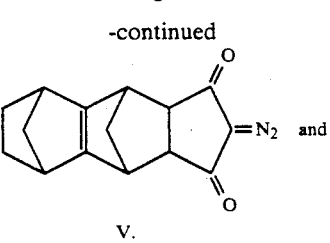
V.

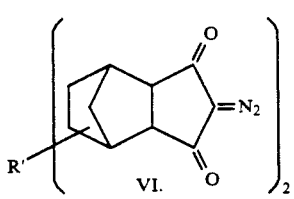
VI.

wherein R is $C_6H_{13}$ or $C_{12}H_{25}$ and R' is $-C_{12}H_{24}-$ or

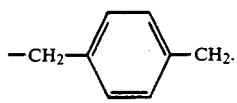

A method for the preparation of each of these compounds is presented in an example below.

UV spectra of these polycyclic compounds containing the structural unit of compound I are quite similar. As a typical example, compound I exhibits a maximum absorption at 248 nm with extinction coefficient of $1.4 \times 10^4$. This peak bleaches either by excimer laser (248 nm) or by high pressure Hg-Xe lamp irradiation (260±25 nm). The two main photolysis products of I in methanol separated by HPLC and identified by mass spectroscopy as VII and VIII, support the photorearrangement mechanism:

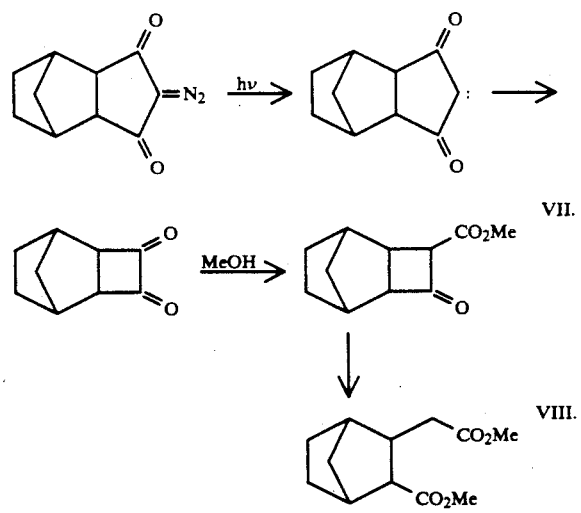

The UV absorptions of these polycyclic compounds are listed in Table 2. The maximum absorptions of these compounds are all about 246 nm with an absorbance coefficient on the order of $10^4$; and these peaks bleach upon deep u.v. irradiation. No detectable absorptions occurred above 300 nm. A remote double bond (compound I compared to II) does not influence the UV absorption significantly. However, these remote unsaturation centers do thermally destabilize the diazo group as indicated by the TGA and DSC data shown in Table 1.

TABLE 1

Thermal Analysis of Several Polycyclic Compounds.
Sample, 10 mg; Heating rate, 10° C./min, in argon)

| Sample | Initial Decomposition Temp., °C. | |
|---|---|---|
| | TGA* | DSC** |
| (structure) | 165 | 160 |
| (structure) | 165 | 155 |
| (structure) | 145 | 139 |

*Represents the temperature of maximum rate of weight loss
**Represents the exothermic peak temperature In the production of the photographic element of the present invention, one coats and dries a photosensitive composition on a suitable substrate. The applied composition contains a solvent, polymer and photosensitizer. The polymer is a water insoluble, aqueous alkaline soluble or swellable polymer. It preferably has a high degree of transparency in the 200-300 nm range. These include 4-tert butylstyrene/maleimide copolymers, 4-tert-butyloxycarbonyloxystyrene/maleimide copolymers and poly(styrene/butyloxycarbonyloxy maleimide).

Preferred are the polymers disclosed in co-pending application U.S. Ser. No. 06/832,116 which is incorporated herein by reference. Examples of such polymers are N-tert-butyloxycarbonyl maleimide/styrene copolymer, N-tert-butyloxycarbonyl maleimide homopolymer, N-tert-butyloxycarbonyl maleimide/vinyl ether copolymers where the vinyl ether is aliphatic from 3 (methyl vinyl ether) to 20 (octadecylvinyl ether) carbon atoms, N-tert-butyloxycarbonyl maleimide/2,4-disubstituted styrene copolymers where the styrene is substituted at the 2 and 4 positions with, independently, $C_1$ to $C_5$ alkyl groups of H. Other polymers which may be used include those in which a phenol containing polymer has the hydroxyl functionalities blocked with an acid-labile group such as poly(tert-butyloxycarbonyloxy-alpha-alkyl styrene) or a copolymer thereof, poly(tert-butyloxycarbonyloxy styrene) or a copolymer thereof, or polymers containing other acidic imide functionalities (—CO—NH—CO—) blocked by an acid labile group such as poly(dimethyl-N-tert-butyloxycarbonyl glutarimide), or polymers containing carboxylic acid functionalities blocked by an acid labile group such as poly(dimethyl-N-tert-butyloxycarbonyl glutarimide), or polymers containing carboxylic acid functionalities blocked by an acid labile group such as poly(tert-butyl p-vinylbenzoate) or a copolymer thereof, poly(tert-butyl methacrylate) or a copolymer thereof, and the like. Other blocking groups may be present on the polymers to yield materials useful for the method of the invention. Examples of such groups may be found in U.S. Pat. application Ser. No. 832,116 filed Feb. 24, 1986 and U.S. Pat. No. 4,491,628, e.g., benzyloxycarbonyl. Still other preferred acid labile polymers are those of co-pending U.S. Pat. application Ser. No. 052,950 filed May 27, 1987. All of the foregoing patents and applications are incorporated herein by reference. Such polymers contain imide groups blocked by a methyol or substituted methylol group and further blocked to form an acetal or ketal.

In general, these polymers can be prepared by standard free radical polymerization techniques from the monomers of the invention, either alone if a homopolymer is desired or by copolymerization with co-monomers.

The polymers of the present invention contain a proportion of acid degradable groups large enough to create a significant solubility difference between irradiated and unirradiated areas. Typically, the mol ratio of co-monomer to substituted methylol maleimide will be between 0 (no co-monomer) and 1.

The comonomer may be chosen from a wide group of vinyl compounds, but most useful are electron-rich vinyl compounds such as styrenes or vinyl ethers. Electron-rich comonomers tend to give an alternating structure upon polymerization with the double blocked methylol maleimide monomer. This has the advantage of creating a uniform polymer for which each molecular chain has approximately the same ratio of monomers without the use of special polymerization techniques such as polymerization to low percent conversion, feeding in one monomer during reaction, or using flow reactors. Preferred comonomers are styrene, alpha-methylstyrene, butyl vinyl ether, and butyl alpha-methylvinyl ether.

The photosensitive composition is formed by blending the ingredients in a suitable solvent composition. In the preferred embodiment the resin is preferably present in the overall composition in an amount of from about 35% to about 98% based on the weight of the solid, i.e. non-solvent parts of the composition. A more preferred range of resin would be from about 80% to about 98% and most preferably from about 82% to about 85% by weight of the solid composition parts. The photosensitizer is preferably present in an amount ranging from about 2% to about 35% based on the weight of the solid, i.e., non-solvent parts of the composition. A more preferred range of the photosensitizer would be from about 2% to about 20% and more preferably from about 15% to about 18% by weight of the solid composition parts. In manufacturing the composition the resin, and photosensitizer are mixed with such solvents as diglyme, propylene glycol alkyl ether acetate, butyl acetate, xylene, ethylene glycol monoethyl ether acetate, and propylene glycol monomethyl ether, among others.

Additives such as colorants, dyes, anti-striation agents, leveling agents, plasticizers, adhesion promoters, speed enhancers, solvents and such surfactants as non-ionic surfactancts may be added to the solution of resin, sensitizer, and solvent before the solution is coated onto a substrate.

Examples of dye additives that may be used together with the photoresist compositions of the present invention include Methyl Violet 2B (C.I. No. 42535), Crystal Violet (C.I. 42555), Malachite Green (C.I. No. 42000), Victoria Blue B (C.I. No. 44045) and Neutral Red (C.I. No. 50040) at one to ten percent weight levels, based on the combined weight of the solid parts of the composition. The dye additives help provide increased resolution by inhibiting back scattering of light off the substrate.

Anti-striation agents may be used up to five percent weight level, based on the combined weight of solids.

Plasticizers which may be used include, for example, phosphoric acid tri-beta-chloroethyl)-ester; stearic acid; dicamphor; polypropylene; acetal resins; phenoxy resins; and alkyl resins at one to ten percent weight levels, based on the combined weight of solids. The plasticizer additives improve the coating properties of the material and enable the application of a film that is smooth and of uniform thickness to the substrate.

Adhesion promoters which may be used include, for example, beta-(3,4-epoxy-cyclohexyl)-ethyltrimethoxysilane; p-methyl-disilane-methyl methacrylate; vinyltrichlorosilane; and gamma-amino-propyl triethoxysilane up to a 4 percent weight level, based on the combined weight of solids.

Speed enhancers that may be used include, for example, picric acid, nicotinic acid or nitrocinnamic acid at a weight level of up to 20 percent, based on the combined weight of resin and solids. These enhancers tend to increase the solubility of the photoresist coating in both the exposed and unexposed areas, and thus they are used in applications when speed of development is the overriding consideration even though some degree of contrast may be sacrificed; i.e., while the exposed areas of the photoresist coating will be dissolved more quickly by the developer, the speed enhancers will also cause a larger loss of photoresist coating from the unexposed areas.

The coating solvents may be present in the overall composition in an amount of up to 95% by weight of the solids in the composition.

Non-ionic surfactants that may be used include, for example, nonylphenoxy poly(ethyleneoxy) ethanol; octylphenoxy(ethyleneoxy) ethanol; and dinonyl phenoxy poly (ethyleneoxy) ethanol at up to 10 percent weight, based on the combined weight of solids.

The prepared resist solution can be applied to a substrate by any conventional method used in the photoresist art, including dipping, spraying, whirling and spin coating. When spin coating, for example, the resist solution can be adjusted for the percentage of solids content in order to provide coating of the desired thickness given the type of spinning equipment utilized and the amount of time allowed for the spinning process. Suitable substrates include silicon, aluminum or polymeric resins, silicon dioxide, doped silicon dioxide, silicon nitride, tantalum, copper, polysilicon, ceramics and aluminum/copper mixtures, gallium arsenide and other Group III/V compounds.

The photoresist coatings produced by the above described procedure are particularly suitable for application to thermally grown silicon/silicon dioxide-coated wafers such as are utilized in the production of microprocessors and other miniaturized integrated circuit components. An aluminum/aluminum oxide wafer can be used as well. The substrate may also comprise various polymeric resins especially transparent polymers such as polyesters. The substrate may have an adhesion promoted layer of a suitable composition such as hexaalkyldisilazane.

After the resist composition solution is coated onto the substrate, the substrate is temperature treated at approximately 20° to 100° C. This temperature treatment is selected in order to reduce and control the concentration of residual solvents in the photoresist while not causing substantial thermal degradation of the photosensitizer. In general one desires to minimize the concentration of solvents and thus this temperature treatment is conducted until substantially all of the solvents have evaporated and a thin coating of the photoresist composition, on the order of a micron in thickness, remains on the substrate. This treatment is normally conducted at temperatures in the range of from about 20° C. to about 100° C. In a preferred embodiment the temperature is conducted at from about 50° C. to about 90° C. A more preferred range is from about 70° C. to about 90° C. This treatment is conducted until the rate of change of solvent removal becomes relatively insignificant. The temperature and time selection depends on the resist properties desired by the user as well as equipment used and commercially desired coating times. Commercially acceptable treatment times for hot plate treatment are those up to about 3 minutes, more preferably up to about 1 minute. In one example, a 30 second treatment at 90° is useful. The coating substrate can then be exposed to actinic radiation, especially deep ultraviolet radiation i.e. 200–300 nm, in any desired pattern, produced by use of suitable masks, negatives, stencils, templates, etc. in a manner well known to the skilled artisan.

The development step may be conducted by immersion in a suitable developing solution. The solution is preferably agitated, for example, by nitrogen burst agitation. The substrates are allowed to remain in the developer until all, or substantially all, of the resist coating has dissolved from the exposed areas. Suitable developers include aqueous alkaline solutions such as those including sodium hydroxide, and tetramethyl ammonium hydroxide as are well known in the art.

After removal of the coated wafers from the developing solution, an optional post-development heat treatment or bake may be employed to increase the coating's adhesion and chemical resistance to etching solutions and other substances. The post-development heat treatment can comprise the oven baking of the coating and substrate below the coating's softening point. In industrial applications, particularly in the manufacture of microcircuitry units on silicon/silicon dioxide-type substrates, the developed substrates may be treated with a buffered, hydrofluoric acid base etching solution. The resist compositions of the present invention are resistant to acid-base etching solutions and provide effective protection for the unexposed resist-coating areas of the substrate.

The following specific examples will provide detailed illustrations of the methods of producing and utilizing compositions of the present invention. These examples are not intended, however, to limit or restrict the scope of the invention in any way and should not be construed as providing conditions, parameters or values which must be utilized exclusively in order to practice the present invention.

EXAMPLE 1

Trichclo (5.2.1.0$^{2.6}$)deca-4-diazo-3,5-dione is prepared as follows:

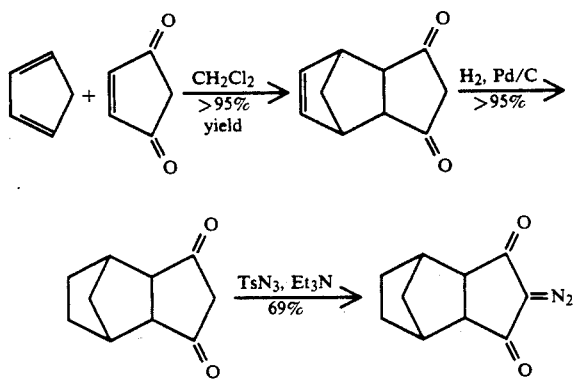

Purification is by column chromatography ($SiO_2$, hexane/ETOAc=3/1) with recrystallization in hexane to produce colorless needle crystals.

$^1$HNMR: 3.12, m, 2H; 2.58, m,2H; 1.63,m,2H; 1.47, m,4H;

IR: 2150 (>=$N_2$), 1660 (>=O);

UV(in $CH_3OH$), lambda max($\epsilon$): 248 nm (14,200); 218 nm (17,000)

EXAMPLE 2

Tricyclo {5.2.1.0$^{2.6}$} deca-8-ene-4-diazo-3,5-dione is prepared as follows:

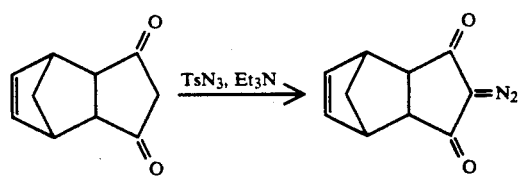

The resultant product appears as colorless grainy crystals.

$^1$H NMR ($CDCl_3$): 6.20, t, J=1.4 Hz, 2H($H_8,H_9$); 3.38, m, 4H($H_1$, $H_7$, $H_2$, $H_6$); 1.85, part of AB, J=8.4 Hz, 1H($H_{10s}$); 1.56, part of AB, J=8.4 Hz, 1H, ($H_{10a}$); IR: 2120 (>=$N_2$), 1675 (>=O), 1595 (>=<); UV (in $CH_3OH$), $\lambda$max ($\epsilon$): 246 nm (13,600); 221 nm, (13,100).

EXAMPLE 3

Compounds III and IV are prepared according to the following scheme.

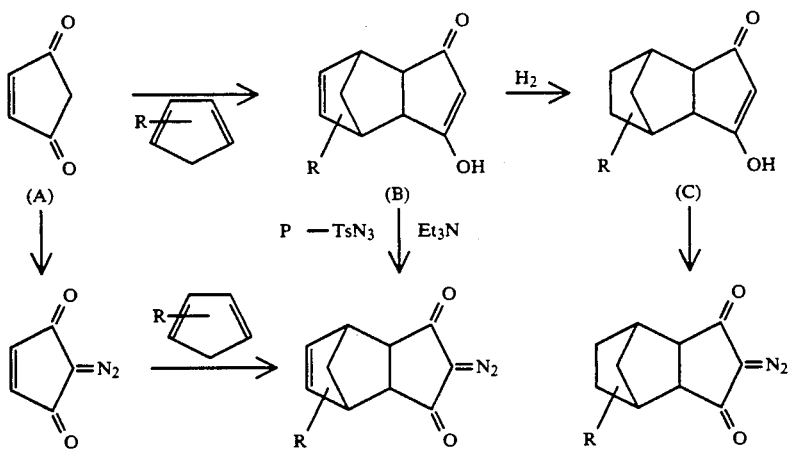

where R is $C_6H_{13}$ or $C_{12}H_{25}$

The alkyl cyclopentadienes are prepared from alkyl halides with cyclopentadienes by published procedures. (See Alder, K.; Ache, H. J. *Chem. Ber.* 95, 1962, 503; and Riemschneider, R.; Reisch, A.; Horak, H. *Monatash*, 91, 1960, 805.) The initially formed 5-alkyl cyclopentadienes are unstable and rearrange to 1-(major) and 2-isomers under normal conditions. Cyclo-addition of the substituted cyclopentadiene with cyclopent-4-ene-1,3-dione (A) gives the cycloadduct (B) usually in high yield. Hydrogenation of (B) is in a parr hydrogenator at 30 psi/room form of beta-keto enol.

Diazo transfer upon (B) or (C) by tosyl azide-triethylamine or polystyrene sulfonyl azide-triethylamine, gives the final product III and IV, respectively. The unsaturated product is also obtained by direct cycloaddition of the diene with 2-diazo-4-cyclopentene-1,3-dione.

EXAMPLE 4

The preparation of compound V is schematically represented as follows:

EXAMPLE 5

The preparation of compounds VI are schematically represented as follows:

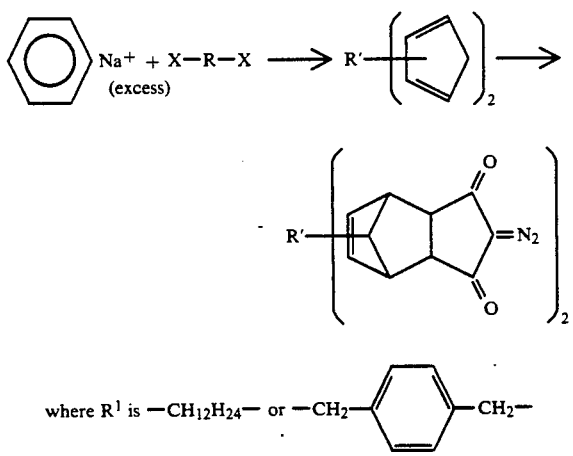

where $R^1$ is $-CH_{12}H_{24}-$ or $-CH_2-\!\!\!\!\!\bigcirc\!\!\!\!\!-CH_2-$

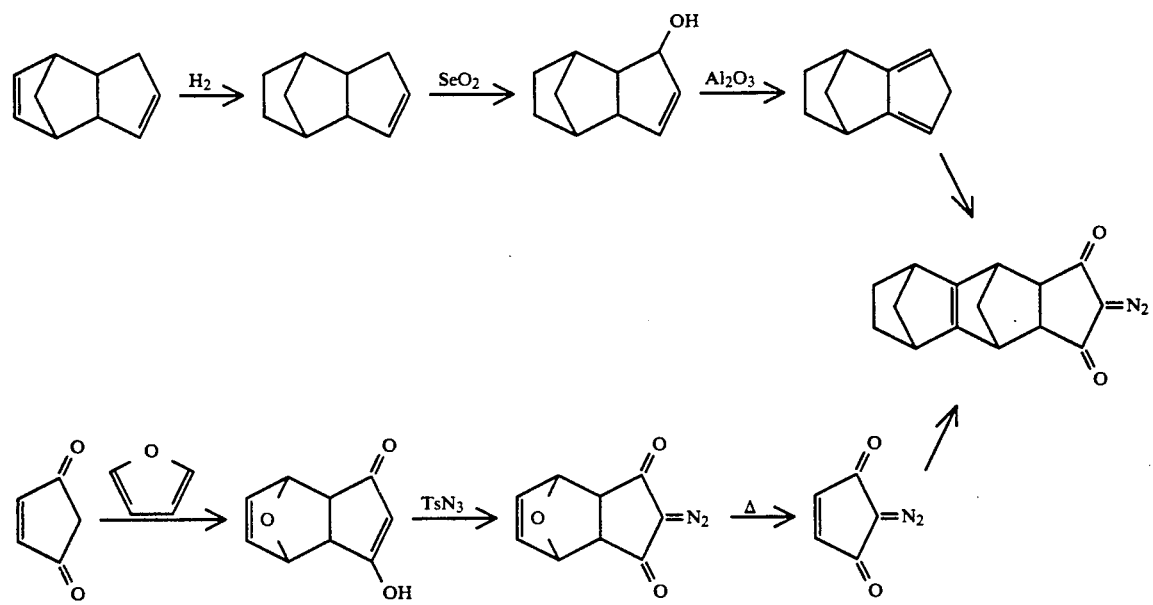

The UV spectral features of some of these compounds are shown in Table 2. The spectra of these compounds are very similar. All have their lambda max at around 246 nm and bleach completely when irradiated.

TABLE 2

| | UV Characteristics (Solution in Methanol) | | | | |
|---|---|---|---|---|---|
| No. | Compound | $\lambda_{max}^1$ | $\epsilon^1$ | $\lambda_{max}^2$ | $\epsilon^2$ |
| 1 | ![structure] | 245 | 14,300 | 213 | 18,100 |
| 2 | ![structure] n-C$_6$H$_{13}$ | 246 | 14,100 | 220 | 12,400 |
| 3 | ![structure] n-C$_6$H$_{25}$ | 245 | 13,600 | 219 | 12,000 |
| 4 | ![structure] | 246 | 13,600 | 221 | 13,100 |
| 5 | ![structure] | 248 | 14,200 | 218 | 17,000 |

EXAMPLE 6

The use of these polycyclic compounds as deep UV positive photosensitizers is demonstrated. The polymer matrix used in the application is a copolymer of maleimide and t-butyl styrene. The sensitizer and polymer in a ratio of 1:7 are dissolved in diglyme (30% solid). This resist composition is spin coated at 3500 rpm onto a hexamethyl disiliazane treated silica wafer to produce a 1.0 μm thick film. The solvent is mostly removed by baking at 80° C. for 40 min. The coated wafer is exposed to 160 mJ/cm² of 260±25 μm light through a step tablet mask. Development in 0.14N KOH to the 30% transmission step in about 40 sec produces clear images, the smallest feature being 1 nm. Some results are listed in Table 3. The film retention may be improved by increasing the molecular weight and the number of diazo groups per molecule of the sensitizer.

| Sensitizer | mJ/cm² | Development Time | Relative Rate | Film Retention, % |
|---|---|---|---|---|
| I | 50 | 20 sec | 1.4:1 | 29 |
| III (R = C$_{12}$H$_{25}$) | 50 | 40 sec | 1.7:1 | 41 |
| V | 50 | 39 sec | 2.5:1 | 60 |
| I | 80 | | 1.8:1 | 44 |
| III (R = C$_{12}$H$_{25}$) | 80 | 31 sec | 2.3:1 | 56 |
| V | 80 | 18 sec | 4.1:1 | 79 |

What is claimed is:

1. A photosensitive composition comprising in admixture:
   (a) from about 65% to about 98% based on the weight of the non-solvent parts of the composition of 4-tert-butylstyrene/maleimide copolymer binder resin; and
   (b) from about 2% to about 35% based on the weight of the non-solvent parts of the composition of a component selected from the group consisting of

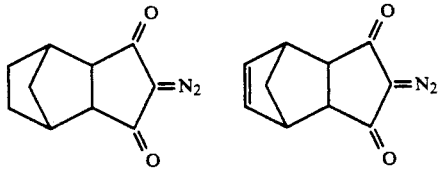

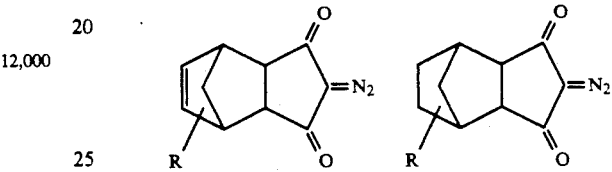

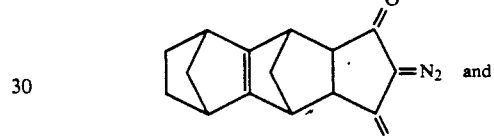

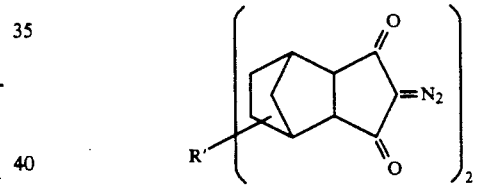

wherein R is C$_6$H$_{13}$ or C$_{12}$H$_{25}$ and R' is —C$_{12}$H$_{24}$— or

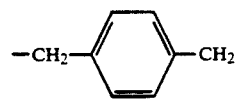

(c) a solvent selected from the group consisting of diglyme, propylene glycol monoalkyl ether and propylene glycol monoalkyl ether acetate in an amount sufficient to form a substantially uniform admixture of the composition components.

2. The composition of claim 1 wherein said binder resin is substantially transparent to ultraviolet radiation in the range of from about 190 to about 300 nm.

3. The composition of claim 1 wherein said composition further comprises one or more compounds selected from the group consisting of colorants, dyes, anti-striation agents, leveling agents, plasticizers, adhesion promoters, speed enhancers, and surfactants.

4. A photographic element which comprises a substrate and a dried photosensitive composition substantially uniformly coated on said substrate which photosensitive composition comprises in admixture;
   (a) from about 65% to about 98% based on the weight of the non-solvent parts of the composition of 4-tert-butylstyrene/maleimide copolymer; and (b) from about 2% to about 35% based on the weight of the non-solvent parts of the composition of a component selected from the group consisting of

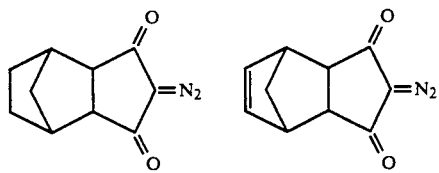

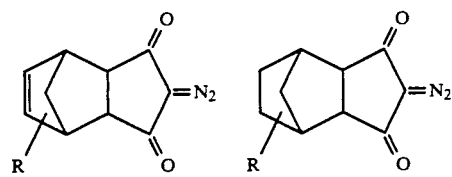

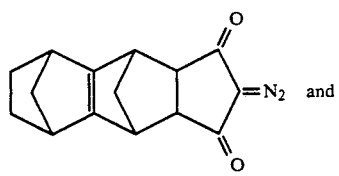

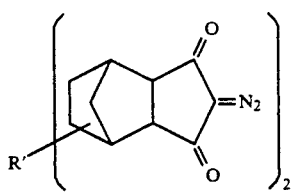

wherein R is $C_6H_{13}$ or $C_{12}H_{25}$ and R' is $-C_{12}H_{24}-$ or

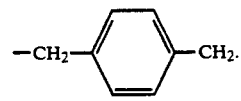

5. The element of claim 4 wherein said binder resin is substantially transparent to ultraviolet radiation in the range of from about 190 to about 300 nm.

6. The element of claim 4 wherein said composition further comprises one or more compounds selected from the group consisting of colorants, dyes, anti-striation agents, leveling agents, plasticizers, adhesion promoters, speed enhancers, and surfactants.

7. The element of claim 4 wherein said substrate is selected from the group consisting of silicon, aluminum or polymeric resins, silicon dioxide, doped silicon dioxide, silicon nitride, tantalum, copper, polysilicon, ceramics, aluminum/copper mixtures, gallium arsenide and Group III/V compounds.

* * * * *